(12) United States Patent
Taylor et al.

(10) Patent No.: US 8,152,835 B2
(45) Date of Patent: Apr. 10, 2012

(54) METHODS FOR THE PLACEMENT OF SUTURES IN TISSUE

(75) Inventors: Eric Taylor, Middletown, CT (US);
Peter Hathaway, Lebanon, CT (US);
Matthew Chowaniec, Middletown, CT (US); Jeffrey Zaruby, Clinton, CT (US)

(73) Assignee: Tyco Healthcare Group LP, North Haven, CT (US)

( * ) Notice: Subject to any disclaimer, the term of this patent is extended or adjusted under 35 U.S.C. 154(b) by 216 days.

(21) Appl. No.: 12/490,719

(22) Filed: Jun. 24, 2009

(65) Prior Publication Data
US 2009/0320861 A1 Dec. 31, 2009

Related U.S. Application Data

(60) Provisional application No. 61/075,406, filed on Jun. 25, 2008.

(51) Int. Cl.
*A61L 17/00* (2006.01)
(52) U.S. Cl. .................................................. 606/228
(58) Field of Classification Search .................. 606/139, 606/144–150, 213, 216, 222–233; 128/898
See application file for complete search history.

(56) References Cited

U.S. PATENT DOCUMENTS

| | | | |
|---|---|---|---|
| 5,364,408 A | 11/1994 | Gordon | |
| 5,860,992 A | 1/1999 | Daniel et al. | |
| 5,895,395 A | 4/1999 | Yeung | |
| 6,997,932 B2 | 2/2006 | Dreyfuss et al. | |
| 7,029,481 B1 | 4/2006 | Burdulis, Jr. et al. | |
| 7,390,328 B2 | 6/2008 | Modesitt | |
| 7,722,631 B2 * | 5/2010 | Mikkaichi et al. | 606/144 |
| 2005/0267531 A1 * | 12/2005 | Ruff et al. | 606/228 |
| 2009/0216251 A1 | 8/2009 | Levine et al. | |

OTHER PUBLICATIONS

Pearl et al., "Natural orifice transluminal endoscopic surgery: past, present and future", Journal of Minimal Access Surgery, Apr.-Jun. 2007, vol. 3, Issue 2.
Swanström, MD, Facs et al., "Natural Orifice Transluminal Endoscopic Surgery: The Future of Gastrointestinal Surgery", The Permanente Journal, Spring 2008, vol. 12, No. 2.

* cited by examiner

*Primary Examiner* — Melanie Tyson

(57) ABSTRACT

A method for the placement of sutures in tissue prior to forming an opening in the tissue, the sutures for use in closing the opening, the method includes the steps of passing a first length of suture through a first portion of a tissue in a first direction relative to a target area to be incised, passing the first length of suture through a second portion of the tissue in the first direction, passing a second length of suture through a third portion of the tissue in a second direction relative to the target area to be incised, passing the second length of suture through a fourth portion of the tissue in the second direction, performing a surgical procedure including forming the opening in the tissue, and applying tension to the first length of suture and the second length of suture to close the opening in the tissue.

11 Claims, 9 Drawing Sheets

METHODS FOR THE PLACEMENT OF SUTURES IN TISSUE

CROSS-REFERENCE TO RELATED APPLICATION

This patent application claims priority to, and the benefit of, U.S. Provisional Application Ser. No. 61/075,406 filed on Jun. 25, 2008, entitled "Re-Directional Stay Suture Technique for Endoluminal Closure" the disclosure of which is herein incorporated by reference in its entirety.

BACKGROUND

1. Technical Field

The present disclosure relates to surgical procedures and, more particularly, to methods for the placement of sutures in tissue.

2. Discussion of Related Art

Various types of surgical procedures are performed to investigate, diagnose, and treat diseases and conditions within patients. Procedures include, for example, the placement of sutures to close surgical access sites or other wounds or joining tissues.

This patent application claims priority to, and the benefit of, U.S. Provisional Application Ser. No. 61/075,406 filed on Jun. 25, 2008, entitled "Re-Directional Stay Suture Technique for Endoluminal Closure", the disclosure of which is herein incorporated by reference in its entirety.

Surgical suturing methods may involve the mechanical movement of a device to drive a suture needle into and/or through tissue. A variety of devices have been developed to allow surgeons to perform suturing techniques in open surgery and minimally invasive surgical procedures and to reduce the amount of time needed for placement of stitches and knot tying. Minimally invasive procedures, such as endoscopic or laparoscopic treatment procedures, are often performed by grasping a suture needle with a needle grasping tool and manipulating the tool to place the suture stitches.

Surgery is evolving beyond current flexible endoscopic and laparoscopic approaches. Natural Orifice Transluminal Endoscopic Surgery (NOTES) represents a new phase of minimally invasive surgery. A goal of NOTES is to avoid the trauma of cutting through the heavily muscled abdominal wall. NOTES involves accessing the abdominal cavity via one of the body's natural orifices (mouth, anus, vagina or urethra). A flexible endoscope is advanced into the peritoneal cavity after puncturing one of the viscera (stomach, colon, vagina or bladder), and the operation is performed using conventional endoscopic instruments. NOTES may offer the benefits of a decreased neurohumoral stress response, decreased immunosuppression, decreased postoperative pain, shorter hospital stay, faster recovery, and a decreased incidence of wound-related and pulmonary complications, and it leaves no visible scars. In addition, the elimination of all abdominal wall incisions may eliminate the risk of wound infection and the incidence of incisional hernia.

Challenges to the advancement and clinical acceptance of NOTES include the need for secure enterotomy closure. Although NOTES appears to offer patient benefits, and may establish itself as a viable alternative to open and laparoscopic surgery for the treatment of many gastrointestinal and abdominal conditions, issues remain. An issue raised by the action of purposely puncturing one of the viscera is how to achieve reliable closure. For safe use of NOTES, there is a need for a closure technique that provides a secure closure of the enterotomy site. A need thus exists for a secure, full-thickness closure technique for closing a defect by endoscopic means.

There is a need for methods for the placement of sutures in tissue to close surgical access sites or join tissues in open surgery, minimally invasive surgical procedures, and the like.

BRIEF DESCRIPTION OF THE DRAWINGS

Objects and features of the presently disclosed methods for the placement of sutures in tissue will become apparent to those of ordinary skill in the art when descriptions of various embodiments thereof are read with reference to the accompanying drawings, of which.

SUMMARY

Figures 1A, 1B:
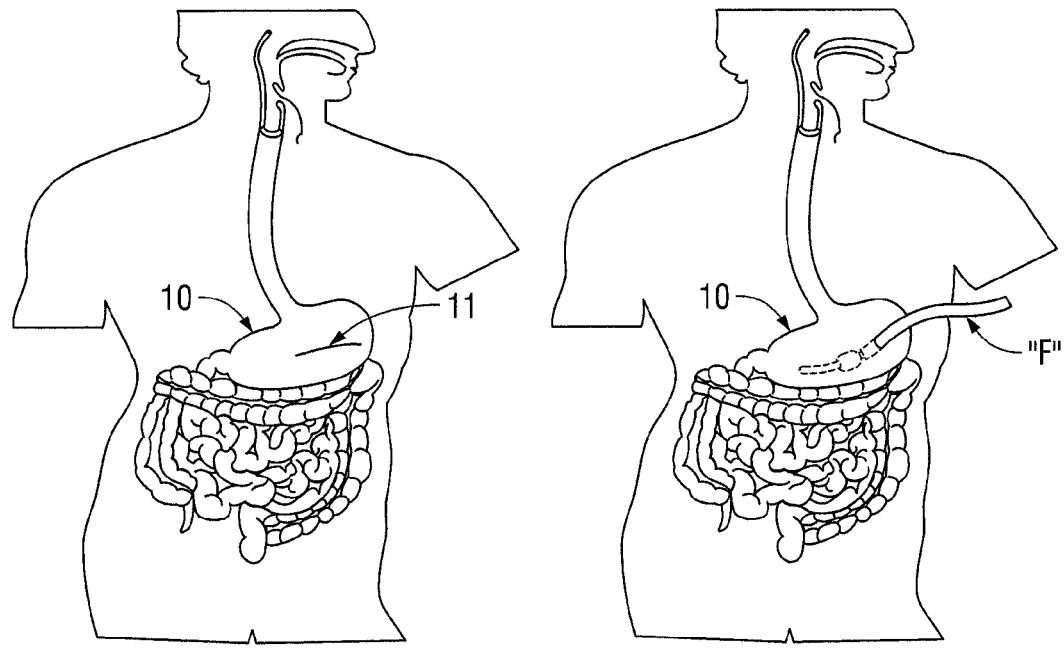
FIGS. 1A and 1B show an open surgery procedure for the placement of a feeding tube through the wall of the abdomen into the stomach.

The present disclosure relates to a method for the placement of sutures in tissue prior to forming an opening in the tissue, the sutures for use in closing the opening, the method including the steps of passing a first length of suture through a first portion of a tissue in a first direction relative to a target area to be incised, passing the first length of suture through a second portion of the tissue in the first direction, passing a second length of suture through a third portion of the tissue in a second direction relative to the target area to be incised, and passing the second length of suture through a fourth portion of the tissue in the second direction. The method also includes the steps of performing a surgical procedure including forming the opening in the tissue, and applying tension to the first length of suture and the second length of suture to close the opening in the tissue.

The present disclosure also relates to a method for the placement of sutures in tissue prior to forming an opening in the tissue, the sutures for use in closing the opening, the method including the steps of providing a needle having a first suture attached thereto, passing the needle having the first suture attached thereto through a first location disposed a first distance from a target area to be incised, the first location being in a first direction from the target area to be incised, and passing the needle having the first suture attached thereto through a second location disposed a second distance greater than the first distance from the target area to be incised, the second location being in the first direction. The method also includes the steps of attaching a second suture to the needle, passing the needle having the second suture attached thereto through a third location disposed the first distance from the target area to be incised, the third location being in a second direction from the target area to be incised, passing the needle having the second suture attached thereto through a fourth location disposed the second distance from the target area to be incised, the fourth location being in the second direction, performing a surgical procedure including forming the opening in the tissue, and applying tension to the first suture in the first direction and to the second suture in the second direction to close the opening in the tissue.

DETAILED DESCRIPTION

Hereinafter, embodiments of the presently disclosed methods for the placement of sutures in tissue will be described with reference to the accompanying drawings. As it is used in this description, "defect" generally refers to a perforation or other opening made through a wall of muscle or other tissue. As it is used in this description, "gastrostomy" refers to a surgical opening into the stomach. As it is used in this description, "suture" generally refers to a material used surgically to join tissues. Sutures may be constructed from a variety of materials including surgical gut, silk, cotton, polyolefins such as polyglycolic acid, glycolide-lactide copolymer, or a wide variety of polyesters derived from polyglycolic acid, or any material or combination of materials adapted for use to join tissues.

FIGS. 1A and 1B show the surgical placement of a feeding tube "F" into a patient's stomach 10. In this procedure, known as a gastrostomy feeding tube insertion, the surgeon makes an incision 11 in the abdominal wall, e.g., at the epigastrium (a region of the abdomen). Feeding tube "F" is inserted through the incision 11 into the stomach 10. Feeding tube "F" may be, for example, a small, flexible, hollow tube with a balloon or special tip. Stomach 10 is stitched closed around the feeding tube "F" and the incision 11 in the abdominal wall is closed. In an open procedure, stay sutures (not shown) are placed on both sides of the incision 11. Tension is placed on the stay sutures, e.g., in such a way that the sutures pull as close to parallel to the tissue as possible. The stay sutures are used to apply tension to the defect in order to properly present the insional edges to help ensure serosa to serosa approximation.

Unlike open procedures, in endoscopic application of stay sutures there is no way to ensure that the force placed on the sutures acts parallel to the tissue. Once the incision defect is created, allowing transluminal passage, it eliminates the ability to maintain insufflation pressure inside the organ, thereby hindering the primary closure. This lack of insufflation distension may make it difficult to locate the defect and/or difficult to operate with any surgical efficiency inside the cavity.

Various embodiments of the present disclosure provide techniques for closing a defect endoscopically that involve the application of a lateral tension at the sides of the defect. Various embodiments provide a method for the placement of sutures in tissue to facilitate the defect's manipulation upon closure. Various embodiments provide a method for the placement of sutures to prepare the defect, prior to its creation, to facilitate the defect's manipulation upon closure and ensure that suturing or wound closure is substantially full thickness. Although various methods described hereinbelow are targeted toward endoscopic application of stay sutures, it is to be understood that disclosed methods for the placement of sutures in tissue may be used in other surgical applications.

Figure 2:
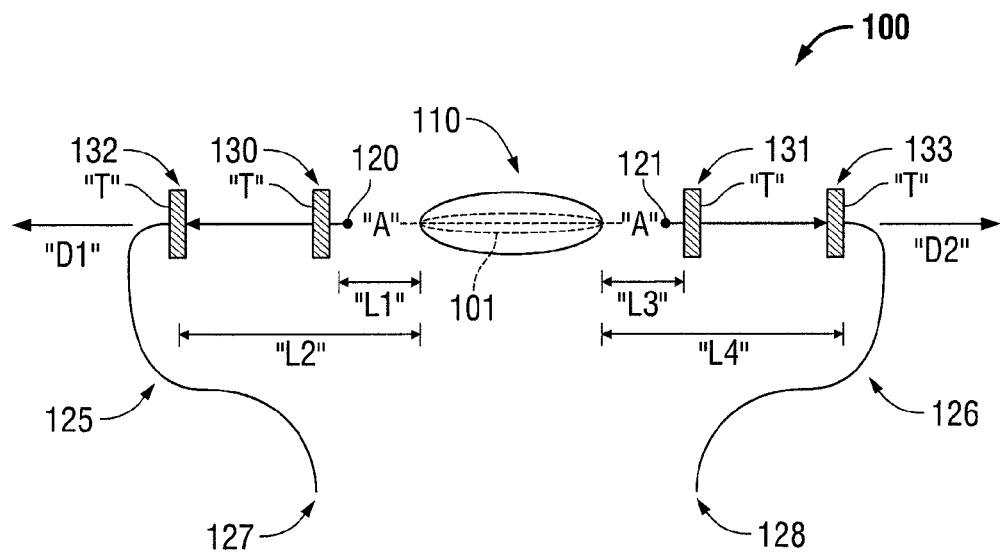
FIG. 2 schematically illustrates a method for the placement of sutures in tissue according to an embodiment of the present disclosure.

Referring to FIG. 2, a method for the placement of sutures in tissue according to an embodiment of the present disclosure is depicted generally as 100. A defect having a generally longitudinal axis "A-A" is depicted as an oval-shaped solid line 110 in FIG. 2. A first suture 125 extends to the left from a first suture termination 120, and a second suture 126 extends to the right from a second suture termination 121. In embodiments, the first and second sutures 125 and 126 extend generally along the longitudinal axis "A-A" of the defect 110. The free end 127 of the first suture 125 and the free end 128 of the second suture 126 may terminate extracorporeally.

First and second sutures 125 and 126 may pass through any number of portions of tissue "T" at any number of locations. As shown in FIG. 2, the first suture 125 may pass through tissue "T" at two locations, 130 and 132, and the second suture 125 may pass through tissue "T" at two locations, 131 and 133. A first pass of the first suture 125 may be made a first length "L1" from the intended incision site, and a second pass of the first suture 125 may be made a second length "L2" from the intended incision site, where the second length "L2" is greater than the first length "L1". A first pass of the second suture 126 may be made a third length "L3" from the intended incision site, and a second pass of the second suture 126 may be made a fourth length "L4" from the intended incision site, where the fourth length "L4" is greater than the third length "L3". In embodiments, the third length "L3" is substantially equal to the first length "L1", and the fourth length "L4" is substantially equal to the second length "L2". The locations of the portions of tissue "T" being passed through by the first and second sutures 125, 126 may be varied from the configuration depicted in FIG. 2.

First and second sutures 125 and 126 may be applied using any suitable device, e.g., mechanical or electromechanical suturing devices, and/or applied by the surgeon using hands. In embodiments, the first and second sutures 125 and 126 are applied using the suturing device commercially available under the trademark ENDO STITCH™ offered by Tyco Healthcare Group LP (now Covidien).

The oval-shaped dotted line 101 illustrated in FIG. 2 represents the effect on tissue "T" when tension is applied to the first suture 125 and the second suture 126. In embodiments, the tension applied to the first suture 125 and the second suture 126 to close the defect 110 in the tissue "T" is applied generally along the longitudinal axis "A-A" of the defect 110.

Figure 3:
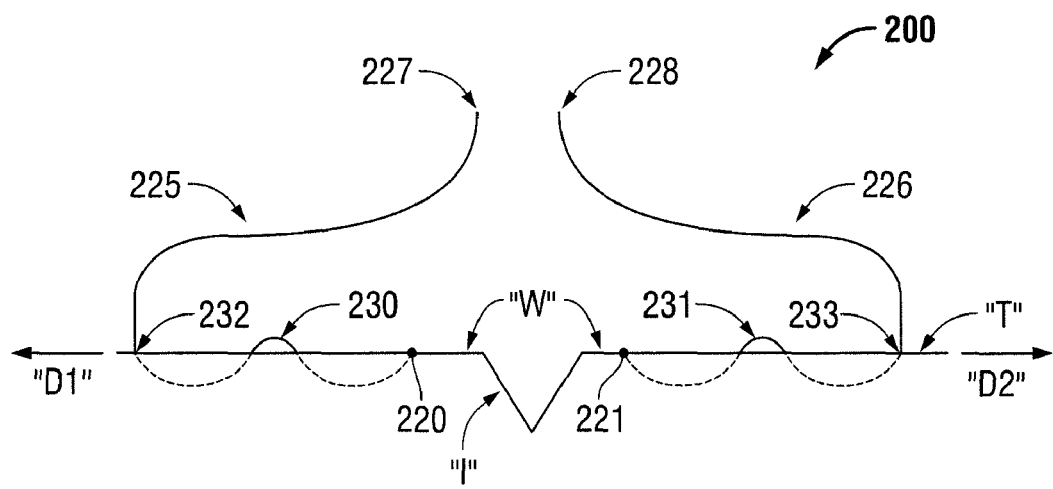
FIG. 3 schematically illustrates a method for the placement of sutures in tissue according to another embodiment of the present disclosure.

Referring to FIG. 3, a method for the placement of sutures in tissue according to another embodiment of the present disclosure is depicted generally as 300. In FIG. 3, a proposed gastric incision is depicted generally as a V-shaped line "I" in the gastric wall "W". In embodiments, a first suture 225 and a second suture 226 are applied by taking two successive "bites" of tissue directed away from the proposed gastric incision "I". In FIG. 3, the first suture 225 extends to the left from a suture termination 220, and the second suture 226 extends to the right from a suture termination 221. Suture termination 220 and the suture termination 221 may be disposed at various distances from the commissure of the proposed gastrostomy. In embodiments, the suture termination 220 and the suture termination 221 are respectively disposed at about 20 millimeters (mm) from the commissure of the proposed gastrostomy.

In embodiments, the first suture 225 passes through tissue (shown generally as line "T" in FIG. 3) at two locations, 230 and 232, and the second suture 226 passes through tissue "T" at two locations, 231 and 233. First and second sutures 225 and 226 may pass through any number of portions of tissue "T" at any number of locations. First suture 225 may include a knotted end 220 and a free end 227. Second suture 226 may include a knotted end 221 and a free end 228. Free end 227 of the first suture 225 and the free end 228 of the second suture 226 may be withdrawn out of the patient's mouth to facilitate extracorporeal manipulation of the gastric wall "W".

Figure 4:
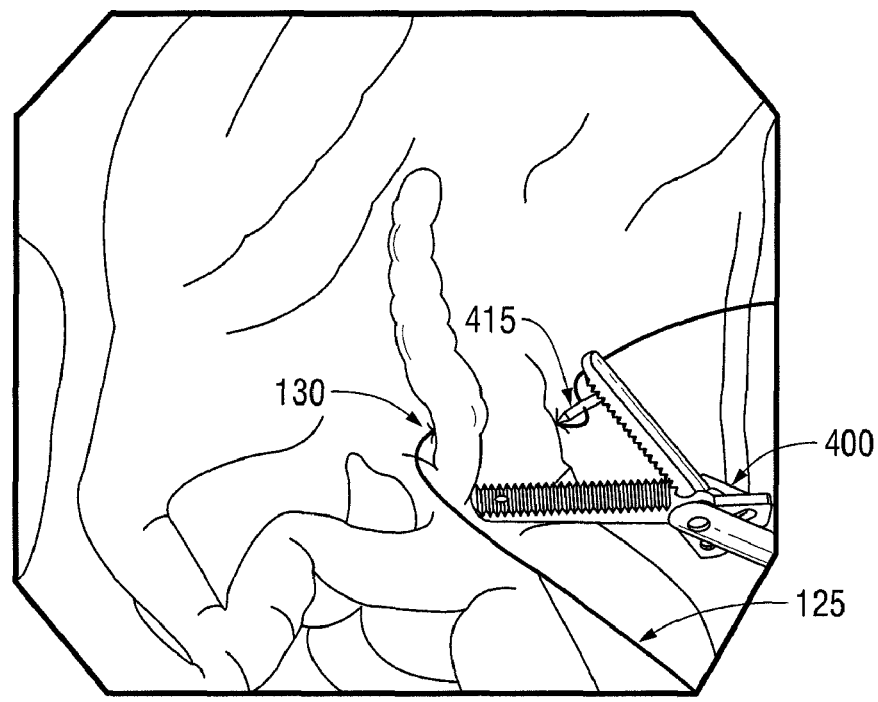
FIG. 4 is a view of biological tissue showing a first suture pass of a first suture that extends extracorporeally from the left side of a gastrostomy according to an embodiment of the present disclosure.
Figure 5:
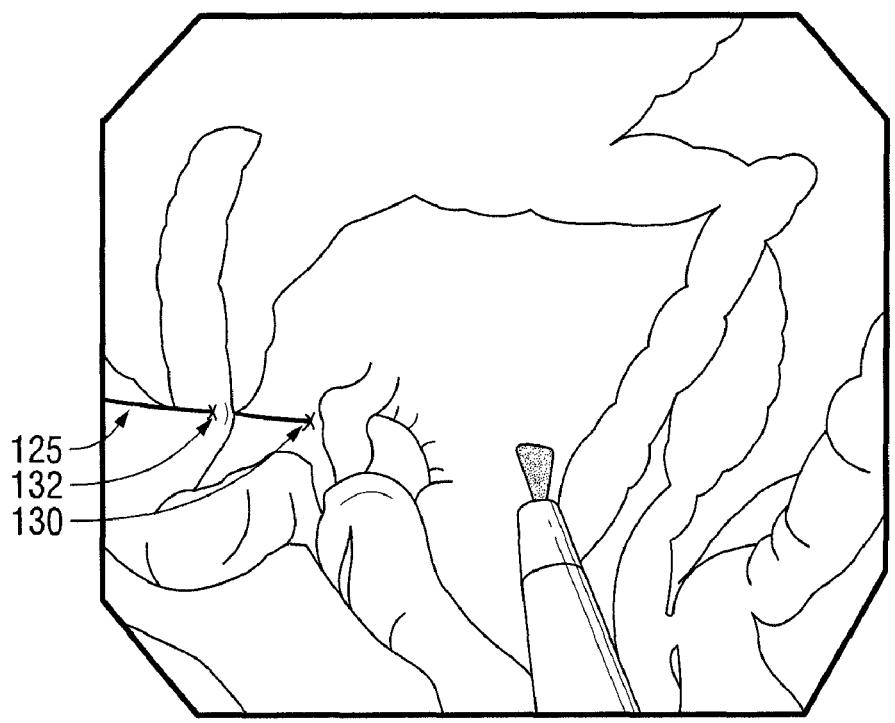
FIG. 5 is a view of the biological tissue of FIG. 4 showing a second suture pass of the first suture according to an embodiment of the present disclosure.

FIG. 4 shows a suturing device 400 including a suture needle 415 to facilitate suture placement and the first suture 125, according to an embodiment of the present disclosure. Suture needle 415 is inserted through tissue portions to form a suture. As shown in FIG. 4, a first suture pass (e.g., through tissue portion 130) of the first suture 125 may extend extracorporeally from the left side of a gastrostomy. FIG. 5 shows a second suture pass (e.g., through tissue portion 132) of the first suture 125, according to an embodiment of the present disclosure.

Figure 6:
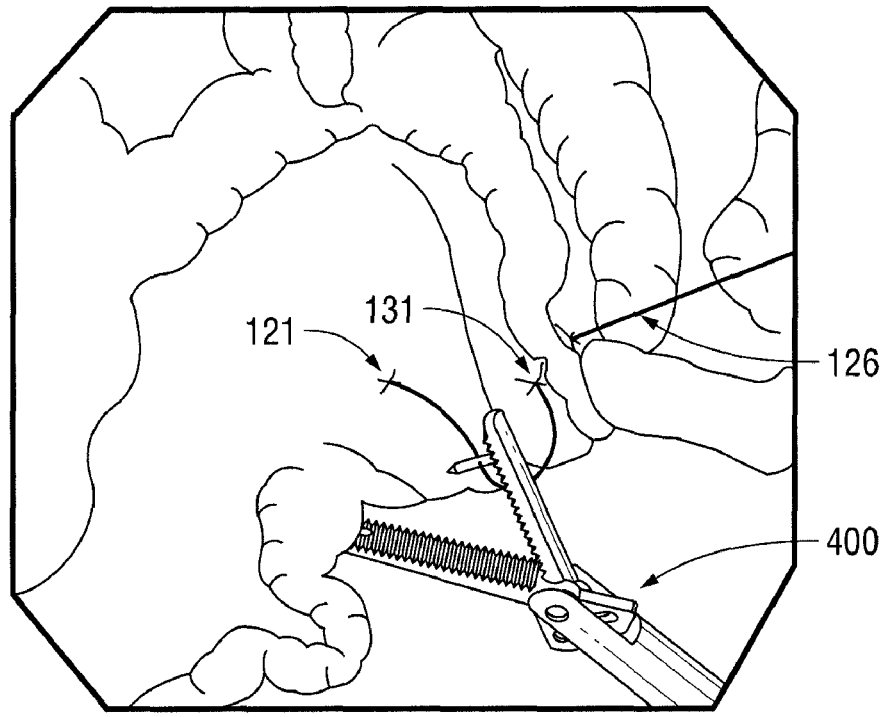
FIG. 6 is a view of biological tissue showing a first suture pass of a second suture that extends extracorporeally from the right side of a gastrostomy according to an embodiment of the present disclosure.

FIG. 6 shows the suturing device 400, the second suture termination 121 and a first suture pass of the second suture 126, according to an embodiment of the present disclosure. In FIG. 6, the first suture pass (e.g., through tissue portion 131) of the second suture 126 extends extracorporeally from the right side of a gastrostomy.

Figure 7:
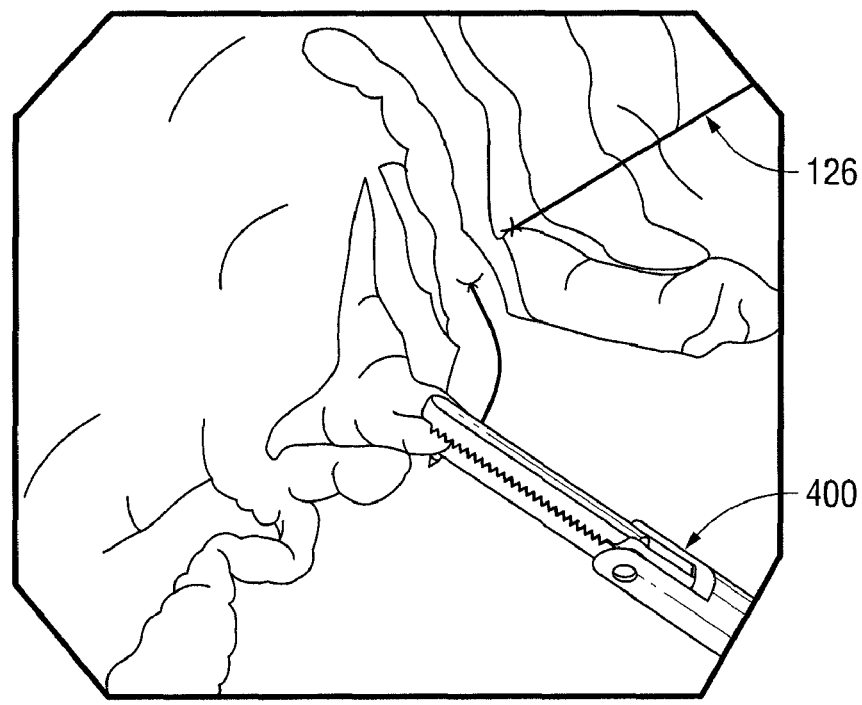
FIG. 7 is a view of the biological tissue of FIG. 6 showing a second suture pass of the second suture according to an embodiment of the present disclosure.

FIG. 7 is a view of the biological tissue of FIG. 6 showing a second suture pass of the second suture. In various embodiments, a second suture pass is used to create a fulcrum by which to translate the tension on the suture to a force that would act parallel to the incision.

Figure 8:
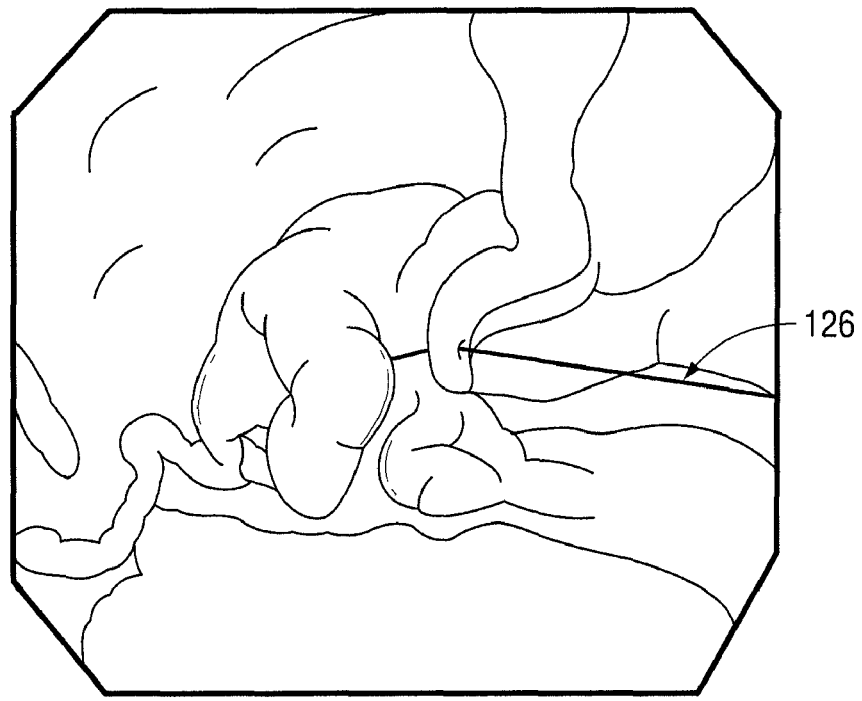
FIG. 8 is a view of the biological tissue of FIG. 6 showing the first and second sutures according to an embodiment of the present disclosure.

The first and second sutures 125 and 126 may terminate extracorporeally. FIG. 8 is a view of the biological tissue of FIG. 6 showing the first and second sutures.

Figure 9:
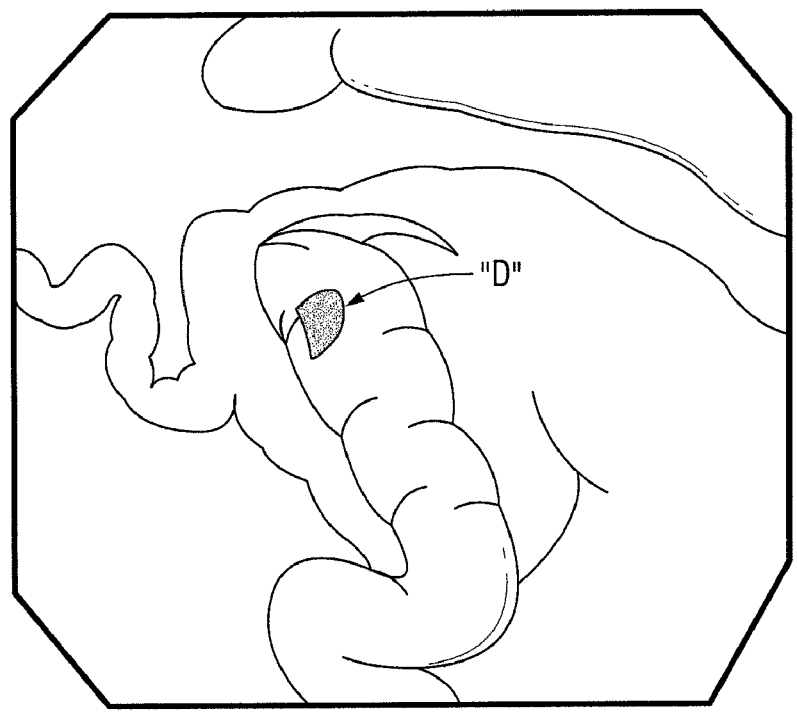
FIG. 9 is a view of biological tissue showing a defect according to an embodiment of the present disclosure.
Figure 10:
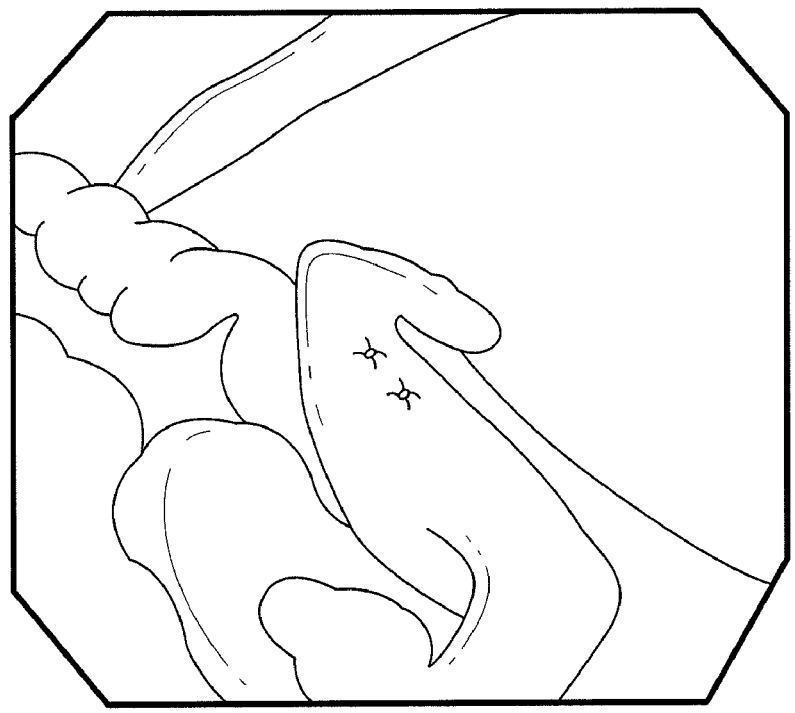
FIGS. 10 and 11 are views of the biological tissue of FIG. 9 showing the defect as the first and second sutures are tensioned according to embodiments of the present disclosure.
Figure 11:
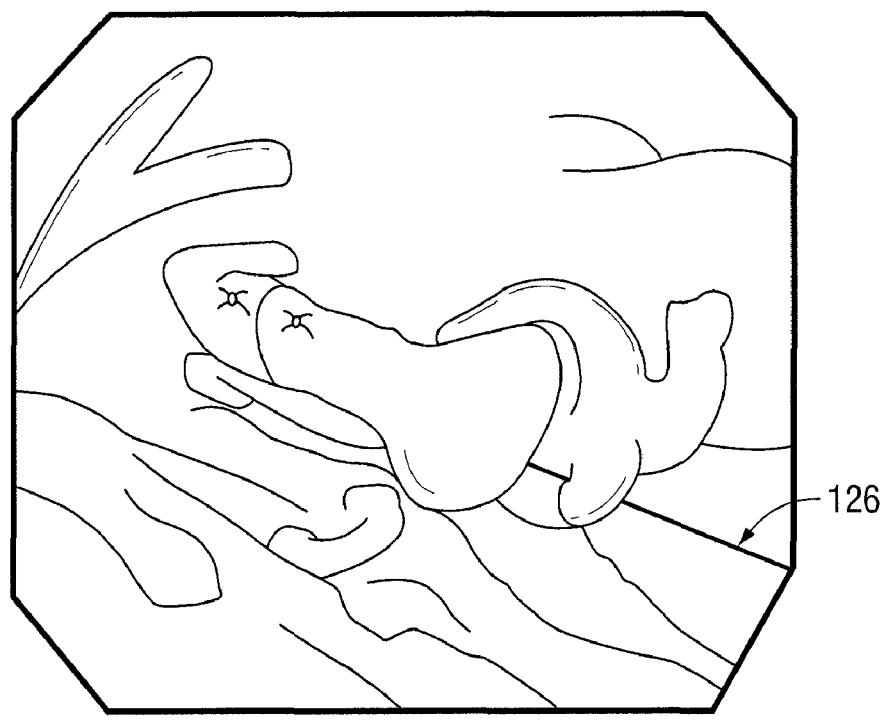

FIG. 9 shows biological tissue and a defect "D" made therein. FIGS. 10 and 11 are views of the biological tissue of FIG. 9 showing the defect "D" as the first and second sutures 225 and 226 are tensioned.

Figure 12:
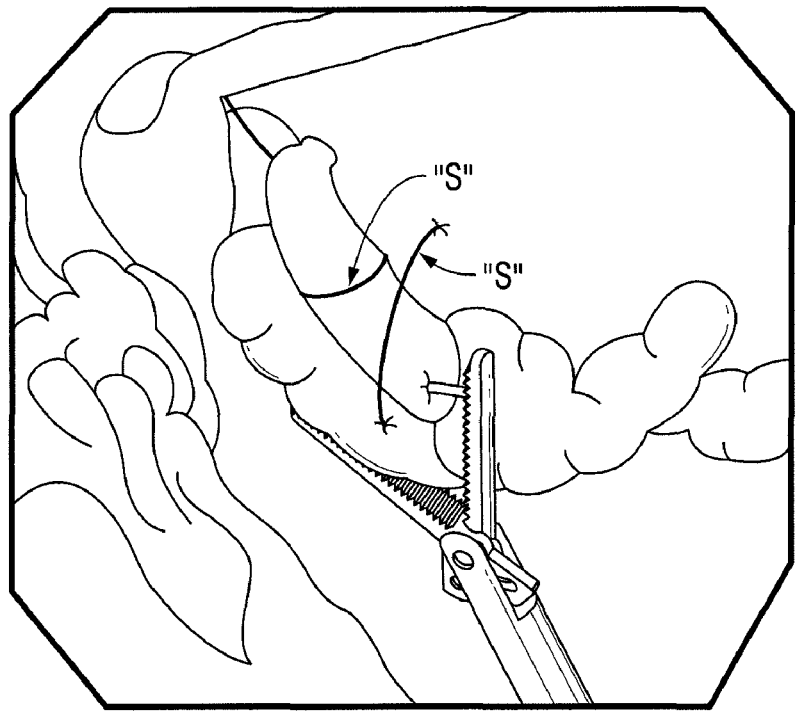
FIGS. 12 and 13 are views of the biological tissue of FIG. 9 showing full-thickness sutures according to embodiments of the present disclosure.
Figure 13:
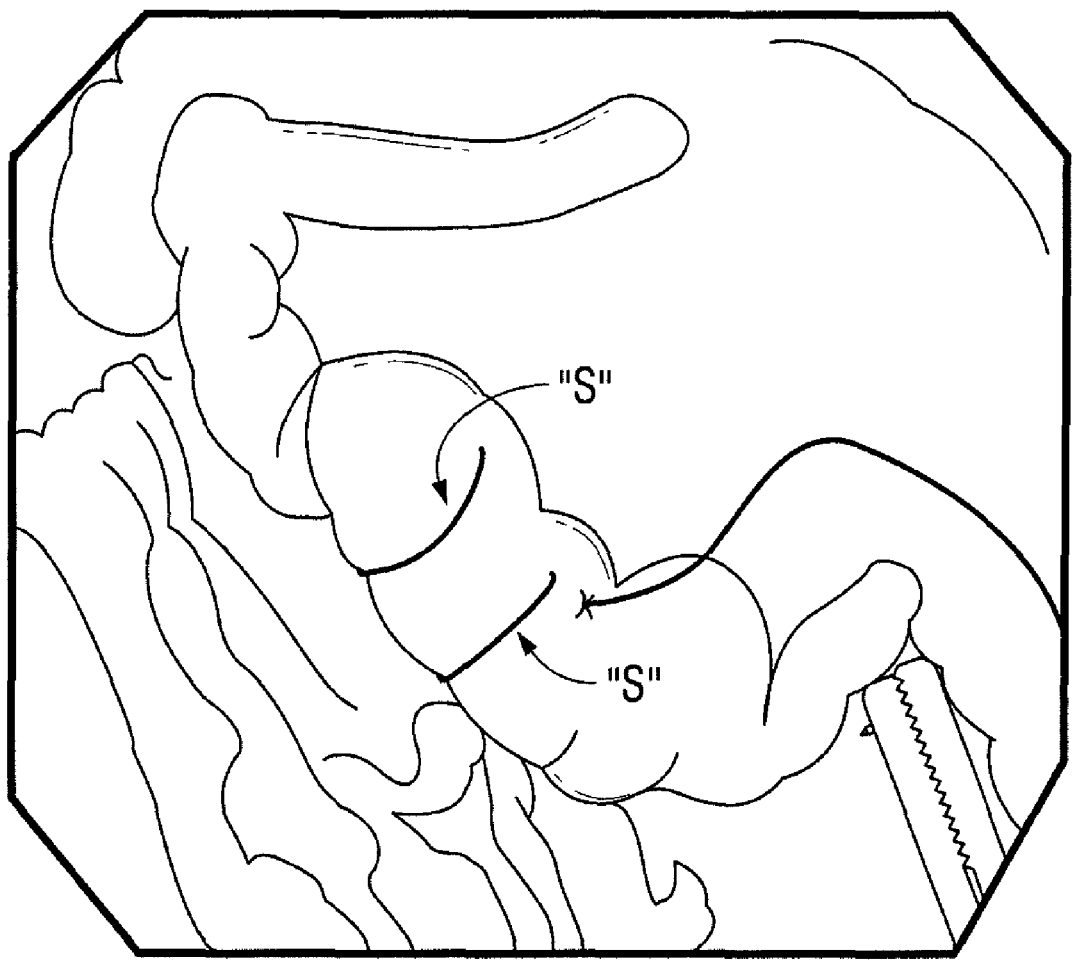

In one embodiment, when the first and second sutures 225 and 226 are pulled tight, it presents the tissue in a "duckbill" type orientation that enables a reliable full thickness suture (e.g., "S" shown in FIGS. 12 and 13) to be placed through both edges of the defect "D". This approximation of the tissues may enable insufflation inside the organ making visualization and manipulation more feasible.

Hereinafter, methods for the placement of sutures in tissue, in accordance with the present disclosure, are described with reference to FIGS. 14 and 15. It is to be understood that the steps of the methods provided herein may be performed in combination and in a different order than presented herein without departing from the scope of the disclosure.

Figure 14:
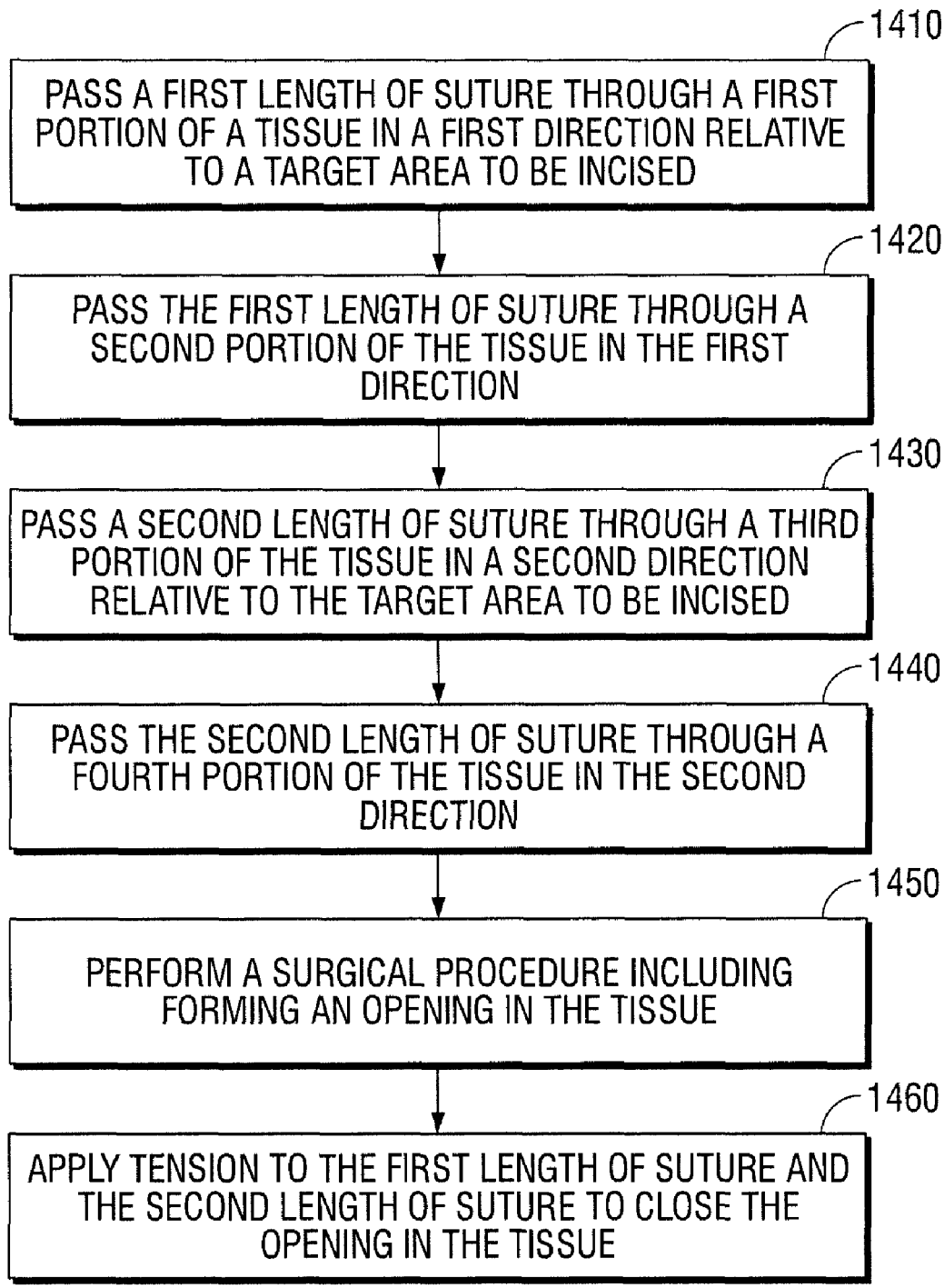
FIG. 14 is a flowchart illustrating a method for the placement of sutures in tissue according to an embodiment of the present disclosure.

FIG. 14 is a flowchart illustrating a method for the placement of sutures in tissue according to an embodiment of the present disclosure. In step 1410, a first length of suture (e.g., 225 shown in FIG. 3) is passed through a first portion (e.g., 230 shown in FIG. 3) of tissue (e.g., "T" shown in FIG. 3) in a first direction (e.g., "D1" shown in FIG. 3) relative to a target area to be incised (e.g., "I" shown in FIG. 3).

In step 1420, the first length of suture is passed through a second portion (e.g., 232 shown in FIG. 3) of the tissue in the first direction.

In step 1430, a second length of suture (e.g., 226 shown in FIG. 3) is passed through a third portion (e.g., 231 shown in FIG. 3) of tissue (e.g., "T" shown in FIG. 3) in a second direction (e.g., "D2" shown in FIG. 3) relative to a target area to be incised (e.g., "I" shown in FIG. 3).

In step 1440, the second length of suture is passed through a fourth portion (e.g., 233 shown in FIG. 3) of the tissue in the second direction.

In step 1450, a surgical procedure is performed that includes forming the opening (e.g., "I" shown in FIG. 3) in the tissue.

In step 1460, tension is applied to the first length of suture and the second length of suture to close the opening in the tissue. In embodiments, the tension applied to the first length of suture and the second length of suture to close the opening in the tissue is applied generally along a longitudinal axis of the opening. After the opening is closed by the application of tension to the first and second lengths of suture, full thickness sutures (e.g., "S" shown in FIGS. 12 and 13) may be placed through edges of the opening.

Figure 15:
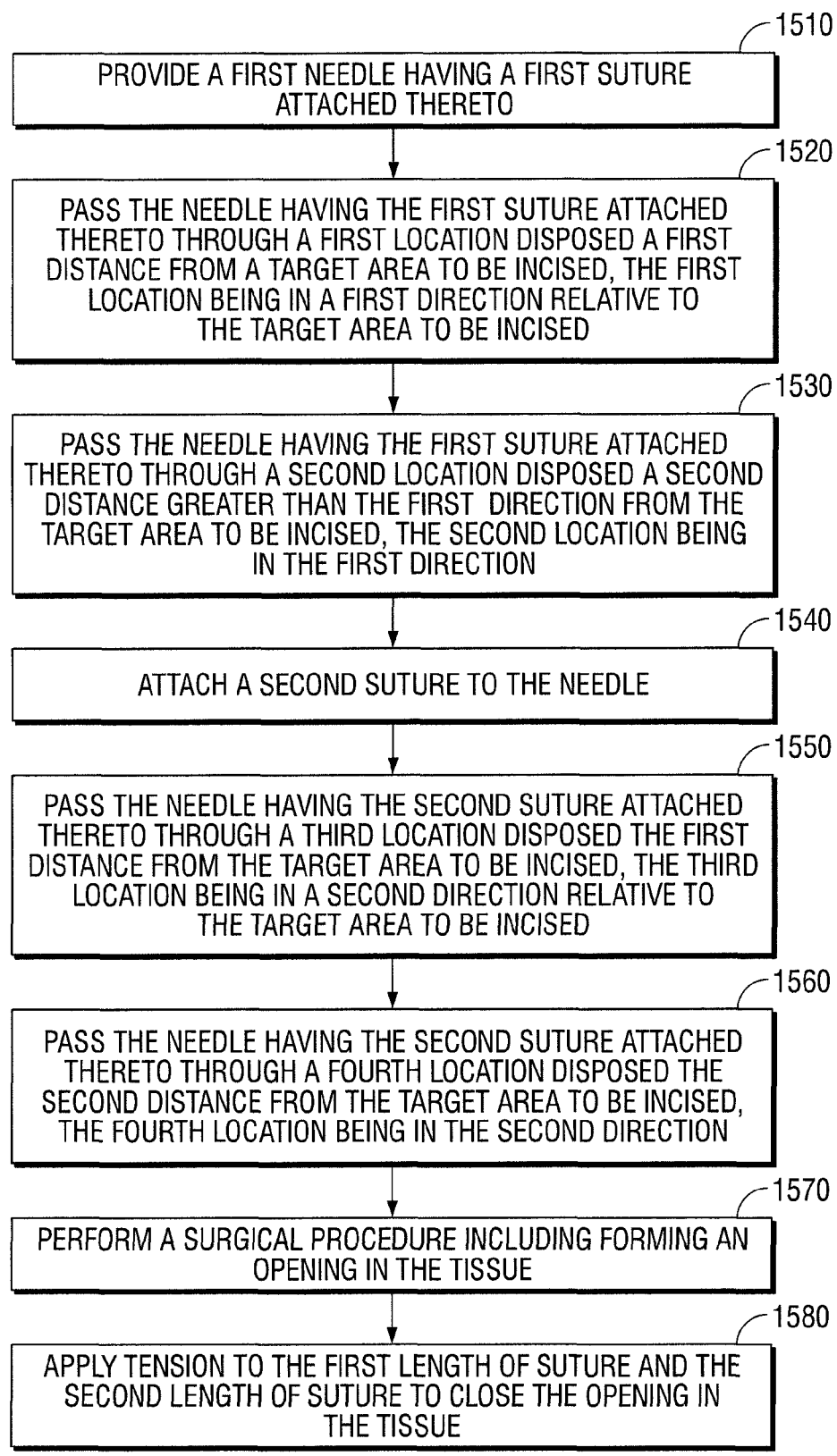
FIG. 15 is a flowchart illustrating a method for the placement of sutures in tissue according to another embodiment of the present disclosure.

FIG. 15 is a flowchart illustrating a method for the placement of sutures in tissue according to another embodiment of the present disclosure. In step 1510, a needle (e.g., 415 shown in FIG. 4) having a first suture (e.g., 125 shown in FIG. 2) attached thereto is provided.

In step 1520, the needle having the first suture attached thereto is passed through a first location (e.g., 130 shown in FIG. 2) disposed a first distance (e.g., "L1" shown in FIG. 2) from a target area to be incised (e.g., 110 shown in FIG. 2), wherein the first location is in a first direction (e.g., "D1" shown in FIG. 2) from the target area to be incised.

In step 1530, the needle having the first suture attached thereto is passed through a second location (e.g., 132 shown in FIG. 2) disposed a second distance (e.g., "L2" shown in FIG. 2) greater than the first distance from the target area to be incised, the second location being in the first direction.

In step 1540, a second suture (e.g., 126 shown in FIG. 2) is attached to the needle. In step 1550, the needle having the second suture attached thereto is passed through a third location (e.g., 131 shown in FIG. 2) disposed a third distance from the target area to be incised, wherein the third location is in a second direction (e.g., "D2" shown in FIG. 2) from the target area to be incised. In embodiments, the length of the third distance is substantially equal to the length of the first distance.

In step 1560, the needle having the second suture attached thereto is passed through a fourth location (e.g., 133 shown in FIG. 2) disposed a fourth distance greater than the third distance from the target area to be incised, wherein the fourth location is in the second direction. In embodiments, the length of the fourth distance is substantially equal to the length of the second distance.

In step 1560, a surgical procedure is performed that includes forming the opening (e.g., 110 shown in FIG. 2) in the tissue.

In step 1560, tension is applied to the first suture in the first direction and to the second suture in the second direction to close the opening in the tissue.

Although embodiments have been described with reference to the accompanying drawings for the purpose of illustration and description, it is to be understood that the inventive processes are not to be construed as limited thereby. It will be apparent to those of ordinary skill in the art that various modifications to the foregoing exemplary embodiments can be made without departing from the scope of the disclosure.

What is claimed is:

1. A method for the placement of sutures in tissue prior to forming an opening in the tissue, the sutures for use in closing the opening, the method comprising the steps of:
   passing a first length of suture through a first portion of a tissue in a first direction relative to a target area to be incised;
   passing the first length of suture through a second portion of the tissue in the first direction;
   passing a second length of suture through a third portion of the tissue in a second direction relative to the target area to be incised;
   passing the second length of suture through a fourth portion of the tissue in the second direction, wherein the first and second lengths of suture extend generally along a longitudinal axis of the opening to be formed in the tissue;
   performing a surgical procedure including forming the opening in the tissue; and
   applying tension to the first length of suture and the second length of suture generally along the longitudinal axis of the opening to close the opening in the tissue.

2. The method of claim 1, further comprising:
   prior to passing the first length of suture through the first portion of the tissue, positioning a suturing device having the first length of suture a first distance from a target area to be incised.

3. The method of claim 2, further comprising:
   prior to positioning the suturing device, selecting the target area to be incised.

4. The method of claim 1, further comprising:
   prior to passing the first length of suture through the second portion of the tissue, positioning the suturing device having the first length of suture a second distance greater than the first distance from the target area to be incised.

5. The method of claim 1, further comprising:
   prior to passing the second length of suture through the third portion of the tissue, positioning a suturing device having the second length of suture a third distance from the target area to be incised.

6. The method of claim 5, wherein the third distance is substantially equal in length to the first distance.

7. A method for the placement of sutures in tissue prior to forming an opening in the tissue, the sutures for use in closing the opening, the method comprising the steps of:
   providing a needle having a first suture attached thereto;
   passing the needle having the first suture attached thereto through a first location disposed a first distance from a target area to be incised, the first location being in a first direction from the target area to be incised;
   passing the needle having the first suture attached thereto through a second location disposed a second distance greater than the first distance from the target area to be incised, the second location being in the first direction;
   attaching a second suture to the needle;
   passing the needle having the second suture attached thereto through a third location disposed a third distance from the target area to be incised, the third location being in a second direction from the target area to be incised, wherein the first and second directions extend generally along a longitudinal axis of the opening to be formed in the tissue;
   passing the needle having the second suture attached thereto through a fourth location disposed a fourth distance greater than the third distance from the target area to be incised, the fourth location being in the second direction;
   performing a surgical procedure including forming the opening in the tissue; and
   applying tension to the first suture in the first direction and to the second suture in the second direction to close the opening in the tissue.

8. The method of claim 7, wherein the third distance is substantially equal to the first distance.

9. The method of claim 8, wherein the fourth distance is substantially equal to the second distance.

10. The method of claim 7, wherein the tension applied to the first length of suture and the second length of suture to close the opening in the tissue is applied generally along a longitudinal axis of the opening in the tissue.

11. A method for the placement of sutures in tissue prior to forming an opening in the tissue, the sutures for use in closing the opening, the method comprising the steps of:
   providing a needle having a first suture attached thereto;
   passing the needle having the first suture attached thereto through a first location disposed a first distance from a target area to be incised, the first location being in a first direction from the target area to be incised;
   passing the needle having the first suture attached thereto through a second location disposed a second distance greater than the first distance from the target area to be incised, the second location being in the first direction;
   attaching a second suture to the needle;
   passing the needle having the second suture attached thereto through a third location disposed a third distance from the target area to be incised, the third location being in a second direction from the target area to be incised;
   passing the needle having the second suture attached thereto through a fourth location disposed a fourth distance greater than the third distance from the target area to be incised, the fourth location being in the second direction;
   performing a surgical procedure including forming the opening in the tissue; and
   applying tension to the first suture in the first direction and to the second suture in the second direction to close the opening in the tissue, wherein the tension applied to the first suture and the second suture to close the opening in the tissue is applied generally along a longitudinal axis of the opening in the tissue.

* * * * *